US010016200B2

(12) United States Patent
Tegels

(10) Patent No.: US 10,016,200 B2
(45) Date of Patent: Jul. 10, 2018

(54) BALLOON BAILOUT AND BIOADHESIVE DELIVERY DEVICE FOR SUTURE BASED CLOSURE AND METHODS

(71) Applicant: St. Jude Medical Puerto Rico LLC, Caguas, PR (US)

(72) Inventor: Zachary J. Tegels, Minneapolis, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 291 days.

(21) Appl. No.: 13/772,834

(22) Filed: Feb. 21, 2013

(65) Prior Publication Data

US 2014/0058440 A1    Feb. 27, 2014

Related U.S. Application Data

(60) Provisional application No. 61/693,148, filed on Aug. 24, 2012.

(51) Int. Cl.
  *A61B 17/08*  (2006.01)
  *A61B 17/00*  (2006.01)
(52) U.S. Cl.
  CPC .......... *A61B 17/08* (2013.01); *A61B 17/0057* (2013.01); *A61B 2017/0065* (2013.01)
(58) Field of Classification Search
  CPC ............ A61B 17/0057; A61B 2017/08; A61B 2017/00645; A61B 2017/00663;
  (Continued)

(56) References Cited

U.S. PATENT DOCUMENTS 3,470,875 A    10/1969 Johnson
3,789,852 A *   2/1974 Kim ................... A61B 17/3439
                                                     604/104
(Continued)

FOREIGN PATENT DOCUMENTS

EP    0818178 A2    1/1998
EP    1158907 A1    12/2001
(Continued)

OTHER PUBLICATIONS

Notification of Transmittal of the International Search Report and the Written Opinion of the International Searching Authority, or the Declaration for International Application No. PCT/US2012/064768, dated Feb. 19, 2013, (18 pages).

(Continued)

*Primary Examiner* — Darwin Erezo
*Assistant Examiner* — Katherine Schwiker
(74) *Attorney, Agent, or Firm* — Dorsey & Whitney LLP

(57) ABSTRACT

A vascular closure assembly is configured to seal a vascular puncture in a vessel. The vascular closure assembly includes a balloon location device and a sealant delivery device. The balloon location device includes an inflation tube and an inflatable balloon positioned at a distal end of the inflation tube and operable, when inflated, between a first position blocking blood flow through the vessel and a second position sealing the puncture from within the vessel. The sealant delivery device includes a sealant delivery tube having a first lumen sized to advance over the inflation tube to the puncture, and a second lumen configured to deliver a volume of sealant to the puncture. The first lumen may include a rapid exchange feature.

14 Claims, 12 Drawing Sheets

(58) Field of Classification Search
CPC .. A61B 2017/0065; A61B 2017/00601; A61B 2017/00615; A61B 2017/00623; A61B 17/08; A61B 17/085; A61B 17/12022; A61B 17/12031; A61B 17/12036; A61B 17/1204; A61B 17/12045; A61B 17/12109; A61B 17/12136; A61B 17/12181; A61B 17/12186; A61B 17/1219; A61B 17/12195; A61B 17/0466; A61B 17/0467; A61B 2017/00575; A61B 2017/00637; A61B 2017/00641; A61B 2017/00654; A61B 2017/00632; A61B 2017/00676; A61B 2017/0081; A61B 2017/088; A61B 2017/086; A61B 2017/1205; A61B 2017/12054; A61B 2017/00592; A61B 2017/00597; A61B 2017/00646; A61B 2017/00659; A61B 2017/00579; A61B 2017/00584; A61B 2017/00588; A61B 2017/00606; A61B 2017/0061; A61B 2017/00619; A61B 2017/00628; A61B 2017/00668; A61B 2017/00672; A61B 2017/12081; A61B 2017/12127; A61B 2017/0409; A61B 2017/047; A61B 2017/00529; A61B 2017/0472; A61B 2017/0474; A61B 2017/0475; A61B 2017/0477; A61B 2017/0483; A61B 1/00112; A61B 1/00082; A61B 1/00119; A61B 1/0014; A61M 2025/0024
USPC ................ 606/213–216, 139, 144, 145, 148; 600/115, 116
See application file for complete search history.

(56) References Cited

U.S. PATENT DOCUMENTS

| | | | |
|---|---|---|---|
| 5,431,666 A | 7/1995 | Sauer et al. | |
| 5,520,702 A | 5/1996 | Sauer et al. | |
| 5,562,686 A | 10/1996 | Sauer et al. | |
| 5,613,974 A | 3/1997 | Andreas et al. | |
| 5,643,292 A | 7/1997 | Hart | |
| 5,674,231 A | 10/1997 | Green et al. | |
| 5,700,273 A | 12/1997 | Buelna et al. | |
| 5,709,692 A | 1/1998 | Mollenauer et al. | |
| 5,728,114 A | 3/1998 | Evans et al. | |
| 5,766,183 A | 6/1998 | Sauer | |
| 5,860,990 A | 1/1999 | Nobles et al. | |
| 5,972,005 A | 10/1999 | Stalker et al. | |
| 6,036,699 A | 3/2000 | Andreas et al. | |
| 6,045,569 A | 4/2000 | Kensey et al. | |
| 6,048,357 A | 4/2000 | Kontos | |
| 6,059,800 A | 5/2000 | Hart et al. | |
| 6,090,130 A | 7/2000 | Nash et al. | |
| 6,136,010 A | 10/2000 | Modesitt et al. | |
| 6,334,865 B1* | 1/2002 | Redmond et al. | 606/213 |
| 6,355,050 B1 | 3/2002 | Andreas et al. | |
| 6,562,052 B2 | 5/2003 | Nobles et al. | |
| 6,623,509 B2 | 9/2003 | Ginn | |
| 6,641,592 B1 | 11/2003 | Sauer et al. | |
| 6,896,692 B2 | 5/2005 | Ginn et al. | |
| 6,911,034 B2 | 6/2005 | Nobles et al. | |
| 6,932,824 B1 | 8/2005 | Roop et al. | |
| 6,964,668 B2 | 11/2005 | Modesitt et al. | |
| 6,969,397 B2 | 11/2005 | Ginn | |
| 7,001,400 B1 | 2/2006 | Modesitt et al. | |
| 7,083,635 B2 | 8/2006 | Ginn | |
| 7,235,087 B2 | 6/2007 | Modesitt et al. | |
| 7,361,183 B2 | 4/2008 | Ginn | |
| 7,390,328 B2 | 6/2008 | Modesitt | |
| 7,553,319 B2 | 6/2009 | Bagaoisan et al. | |
| 7,601,161 B1 | 10/2009 | Nobles et al. | |
| 7,621,937 B2 | 11/2009 | Pipenhagen et al. | |
| 7,686,821 B2 | 3/2010 | Hathaway et al. | |
| 7,731,726 B2 | 6/2010 | Belhe et al. | |
| 7,744,610 B2 | 6/2010 | Hausen | |
| 7,752,853 B2 | 7/2010 | Singh et al. | |
| 7,753,933 B2 | 7/2010 | Ginn et al. | |
| 7,837,696 B2 | 11/2010 | Modesitt et al. | |
| 7,842,047 B2 | 11/2010 | Modesitt et al. | |
| 7,842,048 B2 | 11/2010 | Ma | |
| 7,846,170 B2 | 12/2010 | Modesitt et al. | |
| 7,850,701 B2 | 12/2010 | Modesitt et al. | |
| 7,883,517 B2 | 2/2011 | Pantages et al. | |
| 7,985,240 B2 | 7/2011 | Bagaoisan et al. | |
| 8,029,476 B2 | 10/2011 | Rosenberg et al. | |
| 8,048,092 B2 | 11/2011 | Modesitt et al. | |
| 8,083,768 B2 | 12/2011 | Ginn et al. | |
| 8,192,456 B2 | 6/2012 | Holman et al. | |
| 8,333,787 B2 | 12/2012 | Pipenhagen et al. | |
| 8,506,592 B2 | 8/2013 | Killion et al. | |
| 2001/0012950 A1* | 8/2001 | Nishtala | A61M 25/0662 606/198 |
| 2002/0107530 A1* | 8/2002 | Sauer | A61B 1/0014 606/139 |
| 2004/0093003 A1* | 5/2004 | MacKenzie et al. | 606/190 |
| 2005/0085854 A1 | 4/2005 | Ginn | |
| 2005/0222576 A1* | 10/2005 | Kick | A61B 17/3439 606/104 |
| 2006/0135963 A1* | 6/2006 | Kick | A61B 17/221 606/108 |
| 2006/0212071 A1 | 9/2006 | Ginn et al. | |
| 2008/0065151 A1 | 3/2008 | Ginn | |
| 2008/0147001 A1* | 6/2008 | Al-Marashi et al. | 604/103.04 |
| 2008/0215088 A1* | 9/2008 | Hnojewyj et al. | 606/214 |
| 2008/0319458 A1* | 12/2008 | Reynolds | A61B 17/0057 606/144 |
| 2009/0099578 A1 | 4/2009 | Heneveld et al. | |
| 2009/0287182 A1* | 11/2009 | Bishop et al. | 604/509 |
| 2009/0306685 A1 | 12/2009 | Fill | |
| 2010/0042118 A1* | 2/2010 | Garrison et al. | 606/148 |
| 2010/0211000 A1* | 8/2010 | Killion et al. | 604/57 |
| 2011/0071567 A1 | 3/2011 | Modesitt et al. | |
| 2011/0166595 A1 | 7/2011 | Vidlund et al. | |
| 2011/0282383 A1 | 11/2011 | Vidlund et al. | |
| 2012/0165854 A1* | 6/2012 | Pipenhagen | A61B 17/0057 606/191 |
| 2013/0006299 A1 | 1/2013 | Pipenhagen et al. | |
| 2013/0144316 A1 | 6/2013 | McCrea et al. | |
| 2013/0190808 A1 | 7/2013 | Tegels et al. | |
| 2013/0190812 A1 | 7/2013 | Vidlund | |
| 2013/0190813 A1 | 7/2013 | Tegels et al. | |

FOREIGN PATENT DOCUMENTS

| | | |
|---|---|---|
| EP | 1327419 A2 | 7/2003 |
| EP | 1349501 A2 | 10/2003 |
| EP | 1677682 A2 | 7/2006 |
| EP | 1972282 A2 | 9/2008 |
| EP | 2147640 A2 | 1/2010 |
| EP | 2298180 A1 | 3/2011 |
| WO | 9703613 A1 | 2/1997 |
| WO | 0051498 | 9/2000 |
| WO | 0078226 A1 | 12/2000 |
| WO | 2010081106 A1 | 7/2010 |
| WO | 2011025543 A2 | 3/2011 |

OTHER PUBLICATIONS

Notification of Transmittal of the International Search Report and the Written Opinion of the International Searching Authority, or the Declaration for International Application No. PCT/US2012/066012, dated Feb. 19, 2013, (17 pages).

Notification of Transmittal of the International Search Report and the Written Opinion of the International Searching Authority, or the Declaration for International Application No. PCT/US2012/064770, dated Feb. 19, 2013, (16 pp.).

(56) References Cited

OTHER PUBLICATIONS

PCT Communication Relating to the Results of the Partial International Search for International Application No. PCT/US2013/027052, dated Jun. 12, 2013.
U.S. Appl. No. 13/770,586, filed Feb. 19, 2013.
U.S. Appl. No. 13/770,714, filed Feb. 19, 2013.
International Search Report for International Application No. PCT/US2013/027052, dated Aug. 28, 2013, (6 pp.).
U.S. Appl. No. 13/772,933, filed Feb. 21, 2013.
U.S. Appl. No. 13/773,206, filed Feb. 21, 2013.
U.S. Appl. No. 13/773,062, filed Feb. 21, 2013.
PCT Communication Relating to the Results of the Partial International Search for International Application No. PCT/US2012/041196, dated Sep. 11, 2012.

\* cited by examiner

BALLOON BAILOUT AND BIOADHESIVE DELIVERY DEVICE FOR SUTURE BASED CLOSURE AND METHODS

CROSS-REFERENCE TO RELATED APPLICATION

This application claims the benefit of the filing date of U.S. Provisional Application No. 61/693,148, filed Aug. 24, 2012, and entitled BALLOON BAILOUT AND BIOADHESIVE DELIVERY DEVICE FOR SUTURE BASED CLOSURE AND METHODS, the disclosure of which is incorporated, in its entirety, by reference.

TECHNICAL FIELD

The present disclosure relates generally to methods and systems for sealing tissue punctures, and more particularly, to methods and systems for temporarily occluding fluid flow during a procedure to close the tissue puncture.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

While there are a variety of prior art devices and techniques for closing such punctures, one method includes temporarily sealing the tissue puncture intravascularly using an inflation balloon. A sealing material may be delivered to an outer surface of the tissue to seal the tissue puncture while the temporary seal from the balloon is maintained. Sutures may be used to hold closed the tissue puncture, particularly when dealing with large bore tissue punctures.

SUMMARY

One aspect of the present disclosure relates to a vascular closure assembly configured to seal a puncture in a vessel. The vascular closure assembly includes a balloon location device and a sealant delivery device. The balloon location device includes an inflation tube and an inflatable balloon positioned at a distal end of the inflation tube and operable, when inflated, between a first position blocking blood flow through the vessel and a second position sealing the puncture from within the vessel. The sealant delivery device includes a sealant delivery tube having a first lumen sized to advance over the inflation tube to the puncture, and a second lumen configured to deliver a volume of sealant to the puncture. The first lumen includes a rapid exchange port.

The balloon location device may include a collar positioned proximal of the inflatable balloon, wherein the collar defines a distal position stop for the sealant delivery device. The balloon location device may include a detachable tip positioned at a distal end of the inflation tube, wherein the detachable tip is detachable within the volume of sealant delivered to the puncture upon withdrawal of the balloon location device from the puncture. The sealant delivery device may include an expandable portion positioned proximal of the rapid exchange port, wherein the expandable portion is radially expandable to create a radial seal with a percutaneous incision through which the puncture is accessible.

The vascular closure device may also include a suture placement device operable to position at least one suture across the puncture prior to positioning the balloon location device within the vessel. The suture placement device may position at least one suture through a sidewall of the vessel on opposite sides of the puncture. A knot in the at least one suture may be used to partially seal the puncture while the balloon location device is positioned extending through the puncture.

Another aspect of the present disclosure relates to a method of closing a puncture in a vessel. The method includes providing a balloon location device having an inflation tube and an inflatable balloon positioned at a distal end of the inflation tube, a sealant delivery device, and a suture placement device. The method also includes positioning at least one suture across the puncture with the suture placement device, inserting the balloon through the puncture, inflating the balloon and positioning the inflated balloon in the vessel to occlude blood flow through the vessel, and at least partially sealing the puncture with the at least one suture. The method also includes withdrawing the inflated balloon against an inner surface of the vessel to temporarily seal the puncture, advancing the sealant delivery device along the balloon location device to the puncture, delivering a first volume of sealant through the sealant delivery device to the puncture to seal the puncture, and removing the balloon location device through the first volume of sealant.

The sealant delivery device may include a rapid exchange port, and the method further comprises mounting the sealant delivery device to the balloon location device at the rapid exchange port. The method may include expanding a portion of the sealant delivery device within a percutaneous incision leading to the puncture to seal an entrance to the percutaneous incision. The method may include depositing a detachable tip of the balloon location device within the first volume of sealant. The method may include depositing a second volume of sealant proximal of the first volume of sealant.

The method may also include advancing a sheath through the puncture to enlarge the puncture, and inserting the balloon through the puncture includes advancing the balloon location device through the sheath. The method may include removing the sheath from the puncture prior to at least partially sealing the tissue puncture with the at least one suture. The method may include providing a suture placement device, positioning at least one suture across the tissue puncture with the suture placement device, and tying the at least one suture to partially seal the puncture while the balloon location device is positioned extending through the puncture.

Another aspect of the present disclosure relates to a method of sealing a puncture accessible through a percutaneous incision. The method includes providing a balloon location device having an inflatable balloon, a sealant delivery device having first and second lumens, and a suture placement device. The method also includes positioning at least one suture across the tissue puncture with the suture placement device, inserting the balloon through the puncture and into the vessel, tying the at least one suture to partially seal the puncture while the balloon location device is positioned extending through the puncture, inflating the balloon and withdrawing the inflated balloon against an inner surface of the vessel to temporarily seal the puncture, advancing the sealant delivery device along the balloon location device to the puncture, delivering a first volume of sealant through the sealant delivery device to the puncture to seal the puncture, and removing the balloon location device through the first volume of sealant.

The method may include positioning the inflated balloon in the vessel to occlude blood flow through the vessel before tying the at least one suture. The sealant delivery device may include a rapid exchange port, and the method includes mounting the sealant delivery device to the balloon location device with the rapid exchange port. The balloon location device may include a positioning collar positioned proximal of the balloon and arranged to provide a distal position stop for the sealant delivery device when being advanced along the balloon location device. The method may include radially expanding the sealant delivery device within the percutaneous incision to create a temporary seal with an internal surface of the percutaneous incision. The method may include expanding the puncture with a sheath, advancing the balloon location device through the sheath, and withdrawing the sheath out of the puncture and percutaneous incision prior to tying the at least one suture.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

Throughout the drawings, identical reference numbers designate similar, but not necessarily identical, elements.

DETAILED DESCRIPTION

Figure 1:
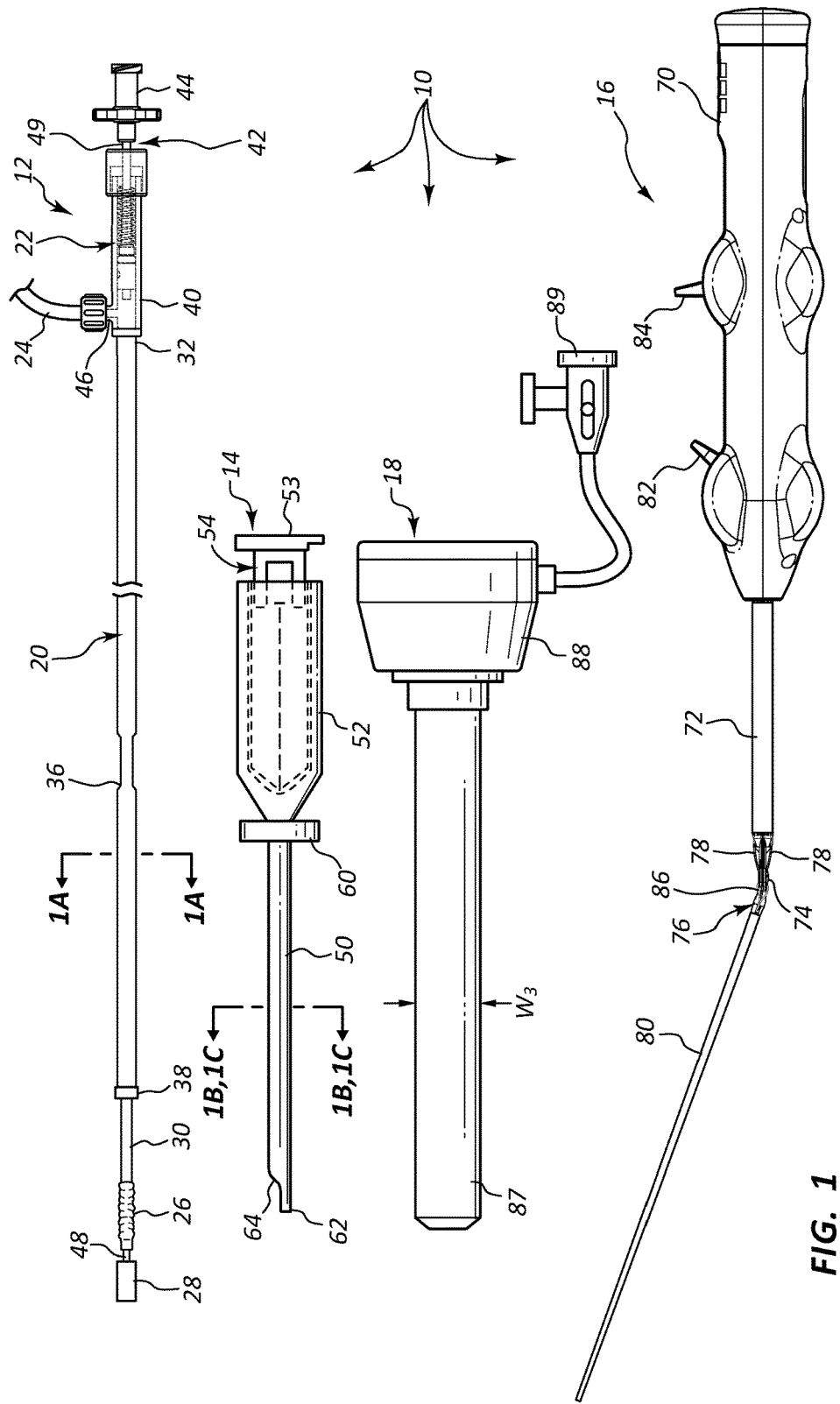
FIG. 1 shows an example vascular closure system in accordance with the present disclosure.

The systems disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

As used in this specification and the appended claims, the terms "engage" and "engagable" are used broadly to mean interlock, mesh, or contact between two structures or devices. Likewise "disengage" or "disengageable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising."

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

An exemplary embodiment of the present disclosure includes a vascular closure system that includes a plurality of devices. In one arrangement, the vascular closure system includes a balloon inflation device, a sealant delivery device, a suture placement device, and a sheath. Other arrangements may include a fewer number of devices as part of the vascular closure system. For example, one arrangement of a vascular closure system includes only a balloon inflation device and a sealant delivery device. In another arrangement, a vascular closure system includes only a balloon inflation device or a sealant delivery device.

The vascular closure system may be particularly useful as part of closing a large bore tissue puncture. Large bore tissue punctures are typically in the range from about 5 to about 30 French, and more particularly from 10 to about 25 French. The sheath of the vascular closure system may help hold open the tissue puncture during treatment of the patient using devices and instruments that are inserted through the sheath. The suture placement device may be used to place at least one suture through tissue adjacent to the tissue puncture. In one example, the suture placement device places two sutures in a wall of a vessel adjacent to a vessel puncture. A suture placement device may be operable percutaneously through a layer of tissue (e.g., skin or fat) that provides access to the vessel puncture.

A balloon inflation device may be inserted through the sheath and into the vessel. In one arrangement, the balloon inflation device operates to position an inflated balloon within the vessel to occlude blood flow through the vessel. The inflated balloon may, in a later step, be retracted or withdrawn proximally to temporarily seal the vessel puncture while delivering a sealant through an exterior of the vessel to seal the vessel puncture from outside of the vessel. In one example, the balloon inflation device temporarily occludes blood flow through the vessel while knots are tied in the suture and positioned across the vessel puncture to partially seal the vessel puncture while the balloon inflation device is positioned extending through the vessel puncture. Suture locking devices may be used in place of knots to apply and maintain tension in the sutures to partially seal the vessel puncture. The free ends of the suture may be cut within the tissue tract so that the free ends of the suture are removed from obstructing further treatment or closure steps.

The sealant delivery device may be advanced into the tissue puncture to deliver a sealant that seals the vessel puncture from outside of the vessel. In one example, the sealant delivery device is advanced along the balloon inflation device. The balloon inflation device may include a stop member such as a collar positioned along its length that provides an axial position stop for the sealant delivery device within the tissue puncture.

A balloon inflation device and sealant delivery device may be configured with rapid exchange features that permit mounting the sealant delivery device to the balloon inflation device at a location spaced between the proximal and distal ends of the balloon inflation device.

The sealant delivery device may include an expandable portion that expands radially outward to temporarily seal the tissue tract during delivery of the sealant to the vessel puncture. The temporary seal provided by the sealant delivery device may help limit backflow of sealant (e.g., a flowable bioadhesive sealant) out of the tissue tract.

The balloon inflation device may be constructed with sufficient length to provide withdrawal of the sheath out of the tissue tract without being removed from the balloon inflation device. The sheath may be withdrawn a distance along the balloon inflation device sufficient for mounting of the sealant delivery device to the balloon inflation device and delivery of the sealant.

The balloon inflation device may also include a detachable sealing tip carried at a distal end of the balloon inflation device. The detachable sealing tip may be deposited within the sealing material that has been deposited by the sealing delivery device. The detachable sealing tip may help seal a tract through the sealing material that has been formed and remains after removal of the balloon inflation device (e.g., the deflated balloon carried by the balloon inflation device) proximally out of the vessel puncture. The balloon inflation device may also be configured to deliver a volume of secondary sealant within the tissue tract. The secondary sealant may be positioned proximal of the first or primary sealant that is delivered into the tissue tract by the sealant delivery device. A secondary sealant deposited by the balloon inflation device may be delivered in place of or in addition to the detachable sealing tip, and may be deposited after detaching the detachable sealing tip within the primary sealant.

Referring now to FIG. 1, an example vascular closure system 10 is shown and described. The vascular closure system 10 includes a balloon inflation device 12, a sealant delivery device 14, a suture placement device 16, and a sheath 18. The devices of the vascular closure system 10 are exemplary only. Other example vascular closure systems may include more or fewer of the devices shown in FIG. 1. For example, the vascular closure system 10 may include only the balloon inflation device 12 and sealant delivery device 14. In other examples, the vascular closure system may include only one of the balloon inflation device 12 and sealant delivery device 14. In at least some embodiments, various features of two or more of the devices 12, 14, 16, 18 may be integrated together as a single device or system.

Figure 1A:
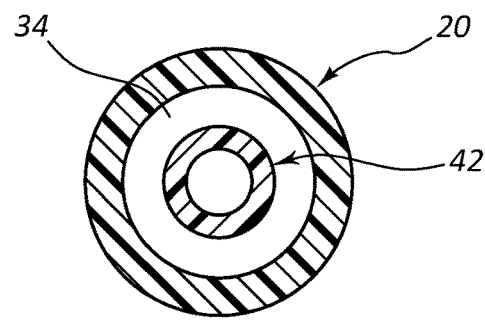
FIG. 1A is a cross-sectional view of a balloon inflation device of the vascular closure system of FIG. 1.

The balloon inflation device 12 may include an inflation tube 20, a balloon location device 22, an inflation source 24, a balloon 26, and a detachable tip 28. The inflation tube 20 may include distal and proximal ends 30, 32, an inflation lumen 34, an exchange port 36, and a collar 38 (see FIGS. 1 and 1A). The balloon 26 may be positioned at the distal end 30 of the inflation tube 20. The detachable tip 28 may be positioned distal of the balloon 26. The inflation source 24 may be used to deliver a volume of inflation fluid through the inflation lumen 34 to the balloon 26.

The balloon location device 22 may include a housing 40, an inner tube 42, an inner tube manifold 44, and an inflation port 46. The inner tube may extend through the housing 40 and the inflation lumen 34 of the inflation tube 20. The inner tube 42 may include a distal end 48 that extends distal of the distal end 30 of the inflation tube 20, and a proximal end 49 that extends proximal of the housing 40. The inner tube manifold 44 may be positioned at the proximal end 49. The detachable tip 28 may be mounted to the distal end 48. The balloon location device 22 may be operable to provide a visual indicator to the operator of, for example, a position, shape, size or condition of the balloon 26. A distal waist of the balloon 26 may be mounted to the distal end 48 of the inner tube 42. Thus, as the balloon 26 inflates and deflates, the inner tube 42 may move axially within the housing 40. The housing 40 may include indices or other markings that help identify axial movement of the inner tube 42 therein. Details concerning operation of a balloon inflation device having a balloon location device are provided in U.S. Patent Application No. 61/590,000 filed on 24 Jan. 2012, and entitled "Balloon Location Device Manifold for Vascular Closure Device and Methods," which is incorporated herein in its entirety by this reference.

Figure 1B:
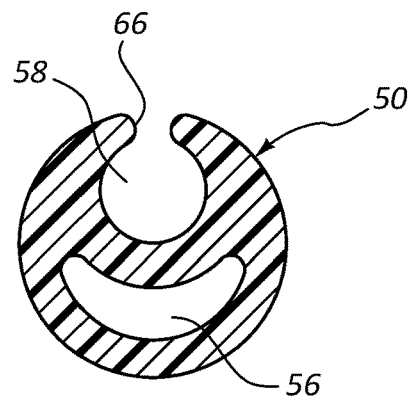
FIGS. 1B and 1C are cross-sectional views of a sealant delivery device of the vascular closure system of FIG. 1
Figure 1C:
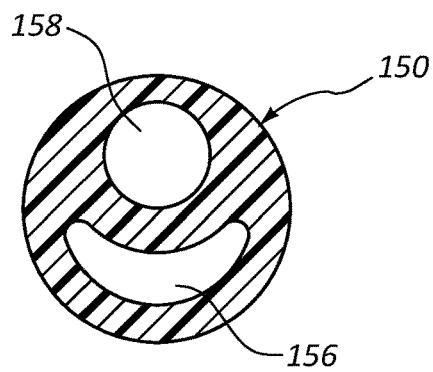

The sealant delivery device 14 may include a sealant shaft 50, a sealant manifold 52, and a sealant mixing device 54. The sealant shaft 50 may include a sealant lumen 56 having a distal end 62, an exchange lumen 58 having a distal opening 64 and side opening 66, and an expansion mechanism 60 (see FIGS. 1 and 1B). The sealant shaft 50 may be mountable to the balloon inflation device 12 at the exchange port 36. In one arrangement, the sealant delivery device 14 may be snap-fit or attached with a lateral insertion through the side opening 66 onto the inflation tube 20 of the balloon inflation device 12. In other arrangements, a sealant shaft 150 includes a sealant lumen 156 and an exchange lumen 158 that does not include a side opening (see FIG. 1C). The interaction between the exchange lumen of the sealant shaft 50 and the exchange port 36 may provide a rapid exchange mounting of the sealant delivery device 14 to the balloon inflation device 12. The rapid exchange features may make it possible to mount the sealant delivery device 14 to the balloon inflation device 12 at a location spaced between proximal and distal ends of the balloon inflation device 12.

Rapid exchange capability may be particularly useful when the balloon inflation device 12 includes a plurality of features at its proximal end such as, for example, the balloon location device housing 40 and inflation port 46 that limit advancement of the sealant delivery device 14 over the proximal end of the balloon inflation device 12.

The rapid exchange features of the balloon inflation device 12 and sealant delivery device 14 may also make it possible to maintain a relatively smaller outer profile for the balloon inflation device 12 for purposes of, for example, delivering the balloon through the vessel puncturing, occluding blood flow through the vessel with the inflated balloon, and temporarily sealing the vessel puncture from within the vessel with the inflated balloon. Adding the features and functionality of the sealant delivery device 14 only after completing these initial functions by the balloon inflation device 12 eliminates the added width otherwise added to the balloon inflation device 12 by the features of the sealant delivery device 14.

Figures 7, 7A:
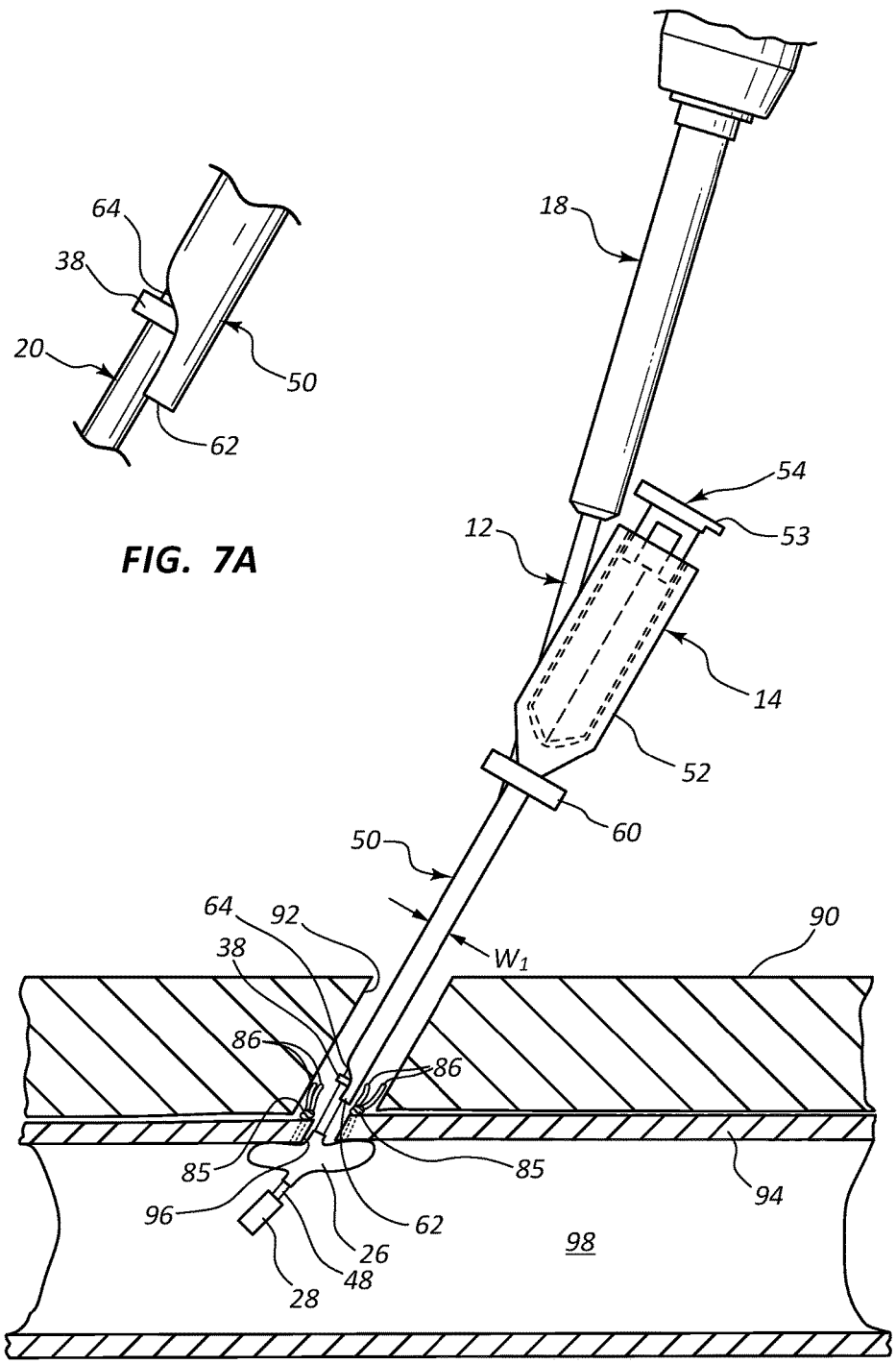
FIG. 7 shows the sealant delivery device of FIG. 1 advanced over the balloon inflation device into the puncture.
FIG. 7A is a close up view of a distal end portion of the sealant delivery device of FIG. 7.
Figure 8:
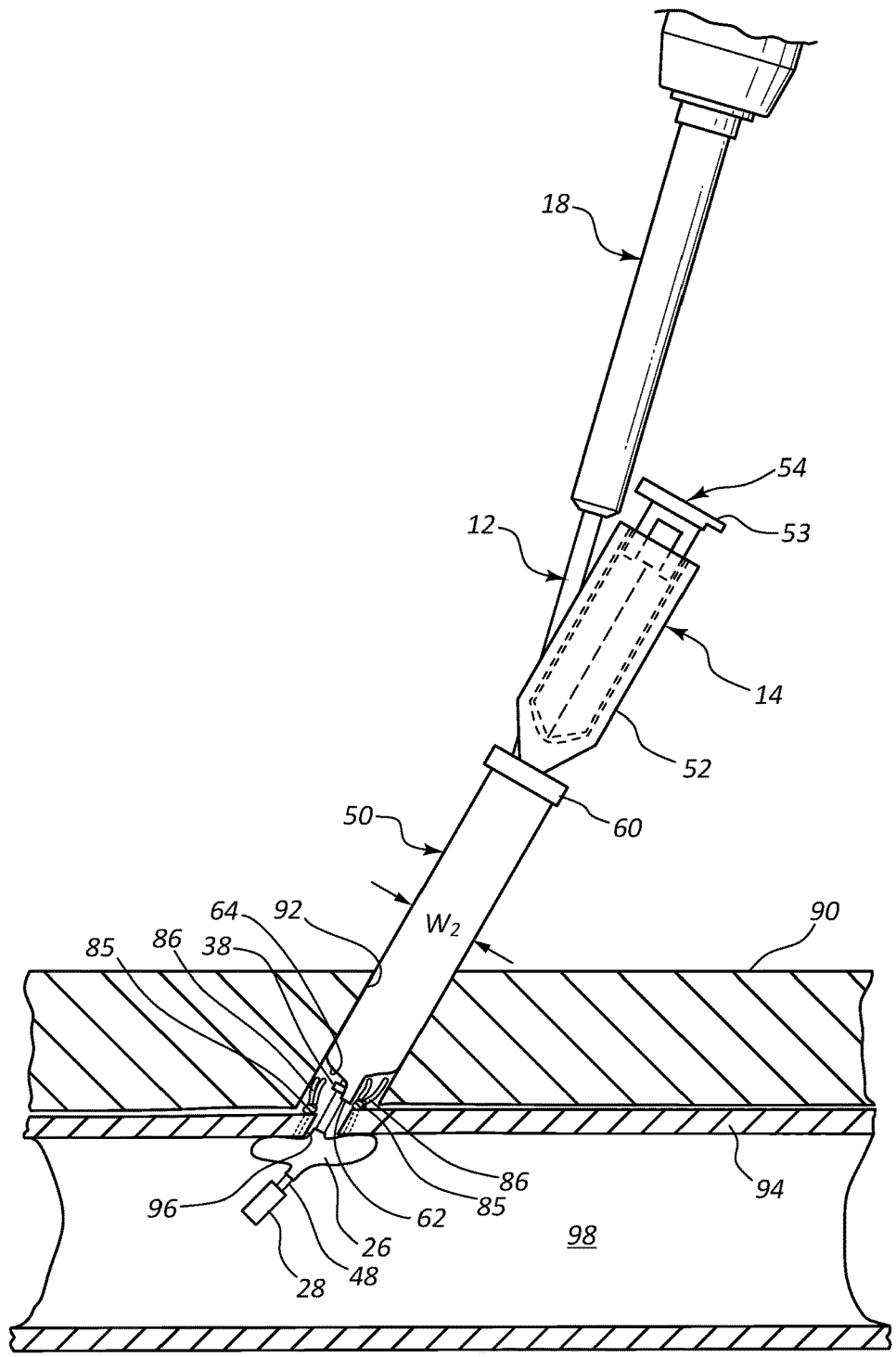
FIG. 8 shows the sealant delivery device of FIG. 7 expanded to seal a tissue tract leading to the puncture.

The sealant shaft 50 may be expandable from a first width $W_1$ (see FIG. 7) to an expanded width $W_2$ (see FIG. 8). The expansion mechanism 60 may operate the sealant shaft 50 between the unexpanded and expanded positions. When in the expanded position shown in FIG. 8, the sealant shaft 50 may form a temporary seal with a tissue tract leading to the vessel puncture. This temporary seal may help limit backflow of sealant delivered by the sealant delivery device 14 out of the tissue tract.

The sealant shaft 50 may be temporarily expanded between the unexpanded and expanded states shown in FIGS. 7 and 8. Various expansion features may be used such as, for example, those features of the expandable sheath shown and described in U.S. Patent Application No. 61/692,980 filed on 24 Aug. 2012 and entitled "Collapsible Sheath and Tapered Dilator for Tissue Puncture Access," which is incorporated herein in its entirety by this reference. Some example expandable structures include an expandable coil, an expandable braided tube, an inflatable balloon or cuff, and an expandable strut.

The sealant mixing device 54 may carry at least one sealant material. In one example, the sealant material carried by the sealant mixing device 54 includes at least two components that remain separated until just prior to delivering the sealant material to the vessel puncture. The sealant mixing device 54 is shown having a plunger 53 used to expel the sealant material from the sealant delivery device 14. Other structures and mechanisms may be used to mix, store, and eject the sealant material through the sealant shaft 50 to a tissue puncture. Example sealant mixing devices and sealant materials are disclosed in U.S. Patent Application No. 61/692,859, filed on 24 Aug. 2012, and entitled "Sealant Storage, Preparation, and Delivery Systems and Related Methods," and U.S. Patent Application No. 61/693,052, filed on 24 Aug. 2012, and entitled "Bioadhesive Mixing and Delivery Device and Methods," which applications are incorporated herein in their entireties by this reference.

Figure 2:
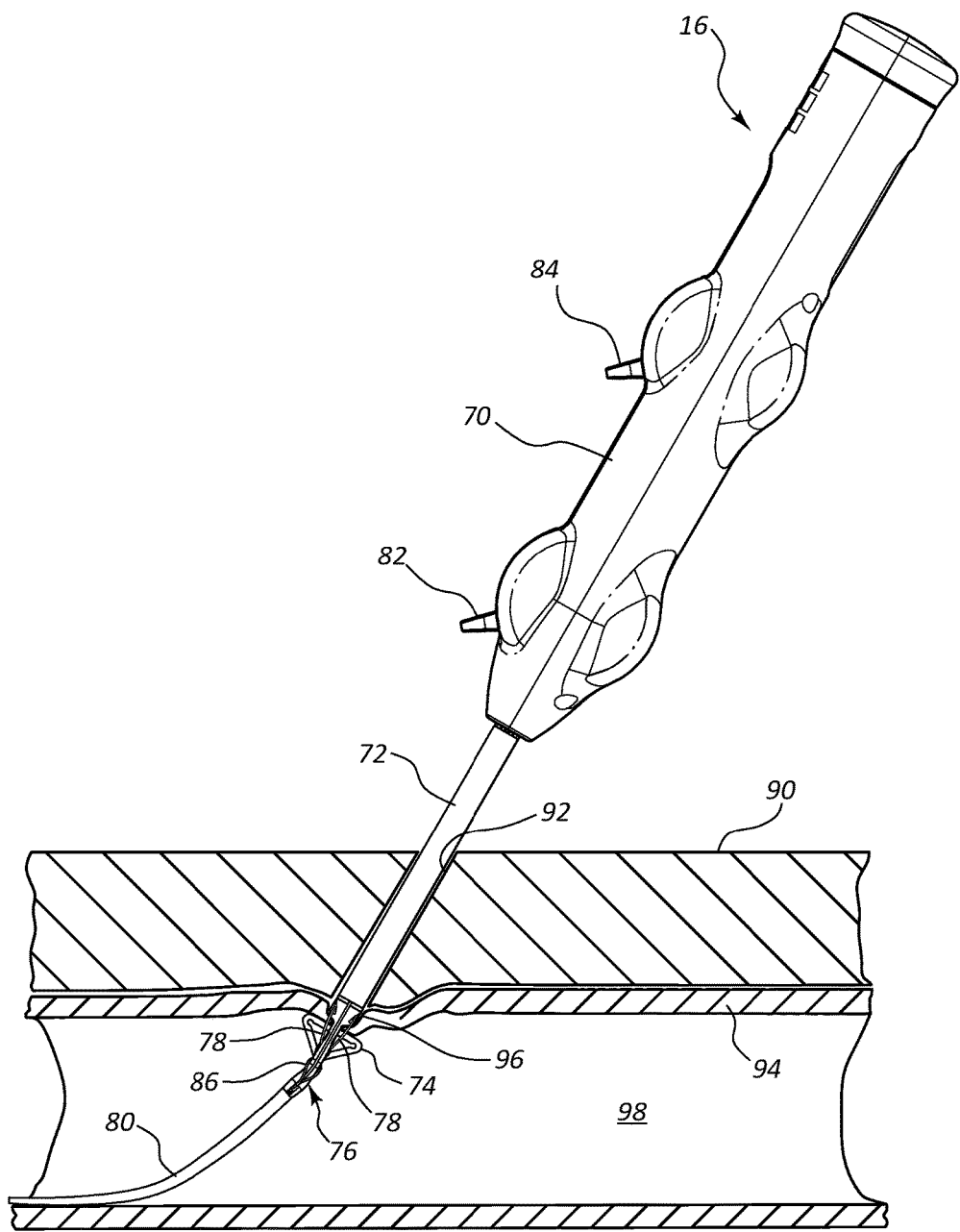
FIG. 2 is a side view of a suture placement device of the vascular closure system of FIG. 1 inserted through a vessel puncture.
Figure 3:
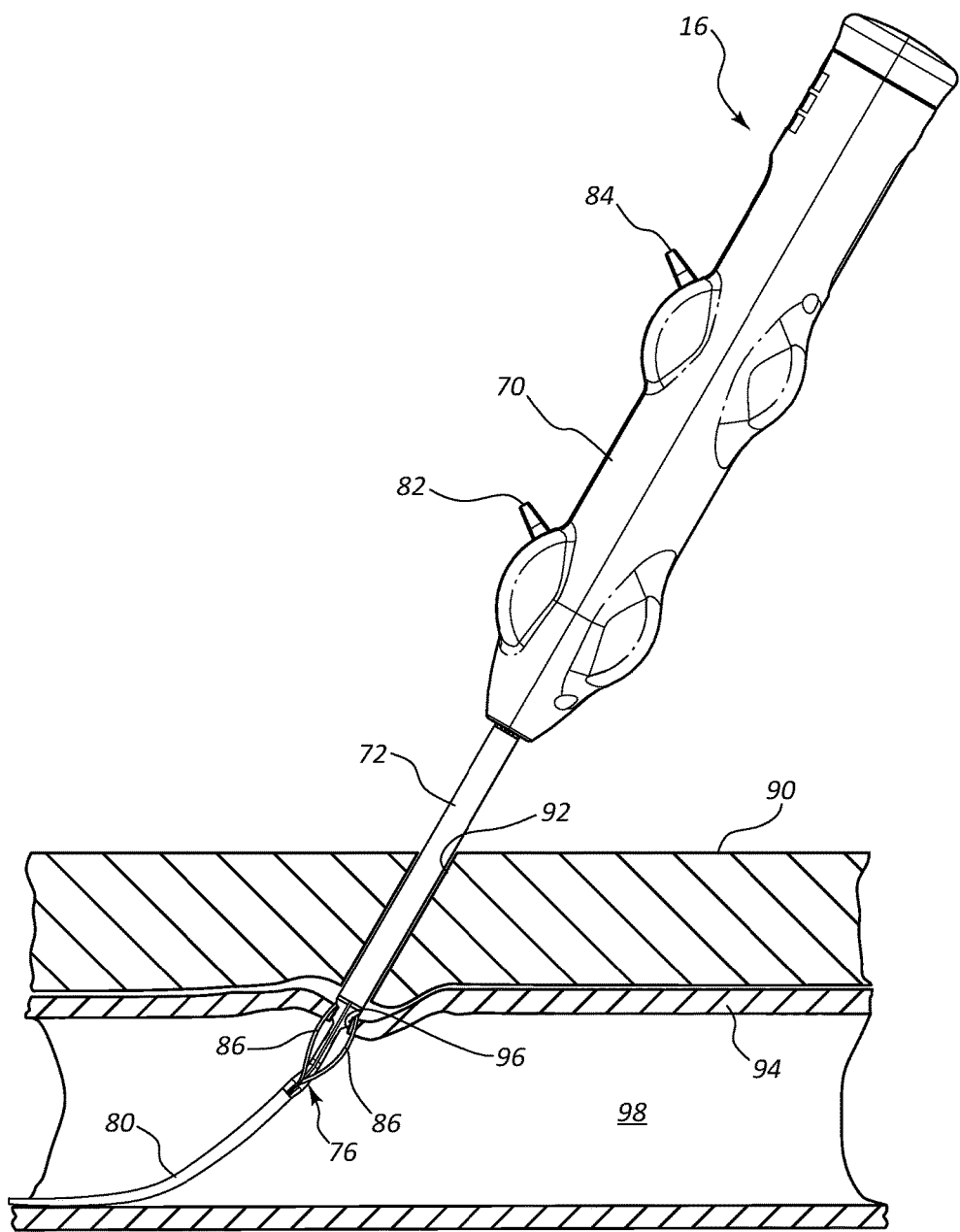
FIG. 3 shows the suture placement device of FIG. 2 operating to place sutures across a wall of the vessel.
Figure 4:
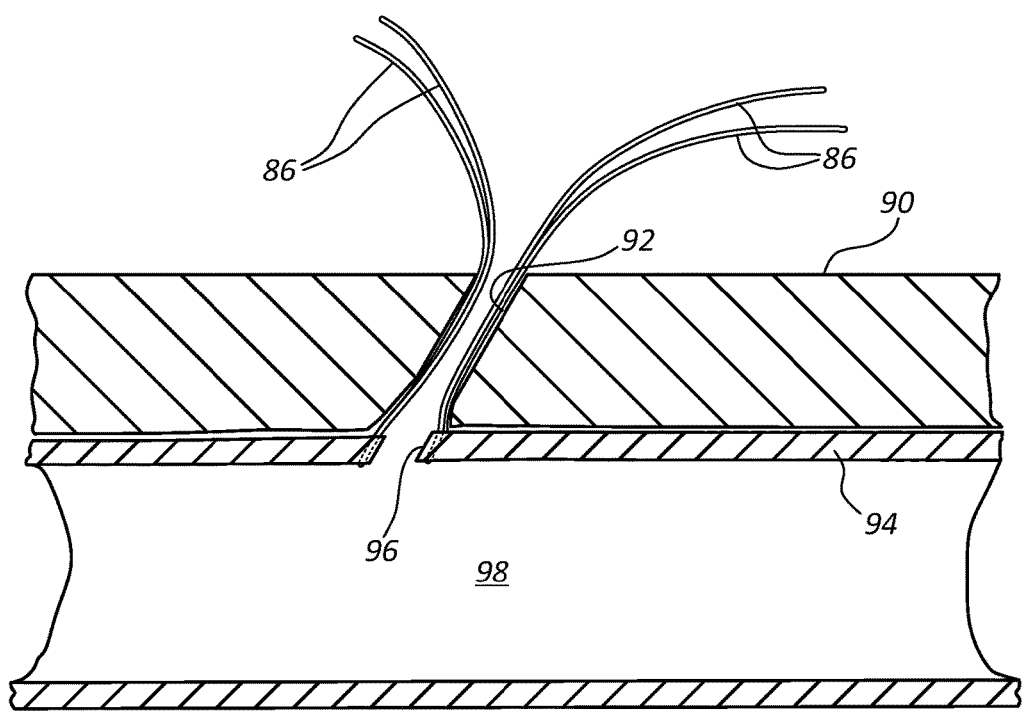
FIG. 4 shows the sutures of FIG. 3 placed across the puncture.

The suture placement device 16 includes a handle 70, an insertion shaft 72, an anchor 74, a suture carrying portion 76, needles 78, and a distal locator tip 80. The handle 70 may include first and second actuators 82, 84. The suture carrying portion 76 may include a plurality of sutures 86. The suture placement device 16 may be operated to place at least one of the sutures 86 across a vessel puncture as shown and described with reference to FIGS. 2-4. The first actuator 82 is operated to move the anchor 74 into an expanded position to capture a vessel wall as shown in FIG. 2. The second actuator 84 is operated to advance the needles 78 through the vessel wall and into contact with the suture carrying portion 76 to capture the sutures 86. The second actuator is operated again to retract the needles 78 to pull the sutures 86 through the vessel wall. The first actuator 82 is operated again to retract the anchor 74 followed by withdrawal of the suture placement device 16 from the vessel puncture to leave behind the sutures 86 positioned extending through the vessel wall as shown in FIG. 4.

Details concerning operation of an example suture placement device is shown and described in U.S. Patent Application No. 61/494,345, filed on 7 Jun. 2011, and entitled "Large Bore Closure Device and Methods," which is incorporated herein in its entirety by this reference. Many types of suture placement devices may be used to position at least one suture across the vessel puncture. Typically, the suture placement device 16 is used to place the sutures across the vessel puncture prior to other treatment and operational steps. For example, the suture placement device 16 may be operated as shown in FIGS. 2-4 to place the sutures 86 across the vessel puncture prior to inserting the sheath 18 to expand the tissue tract in vessel puncture and treating the patient through the vessel.

Figure 6:
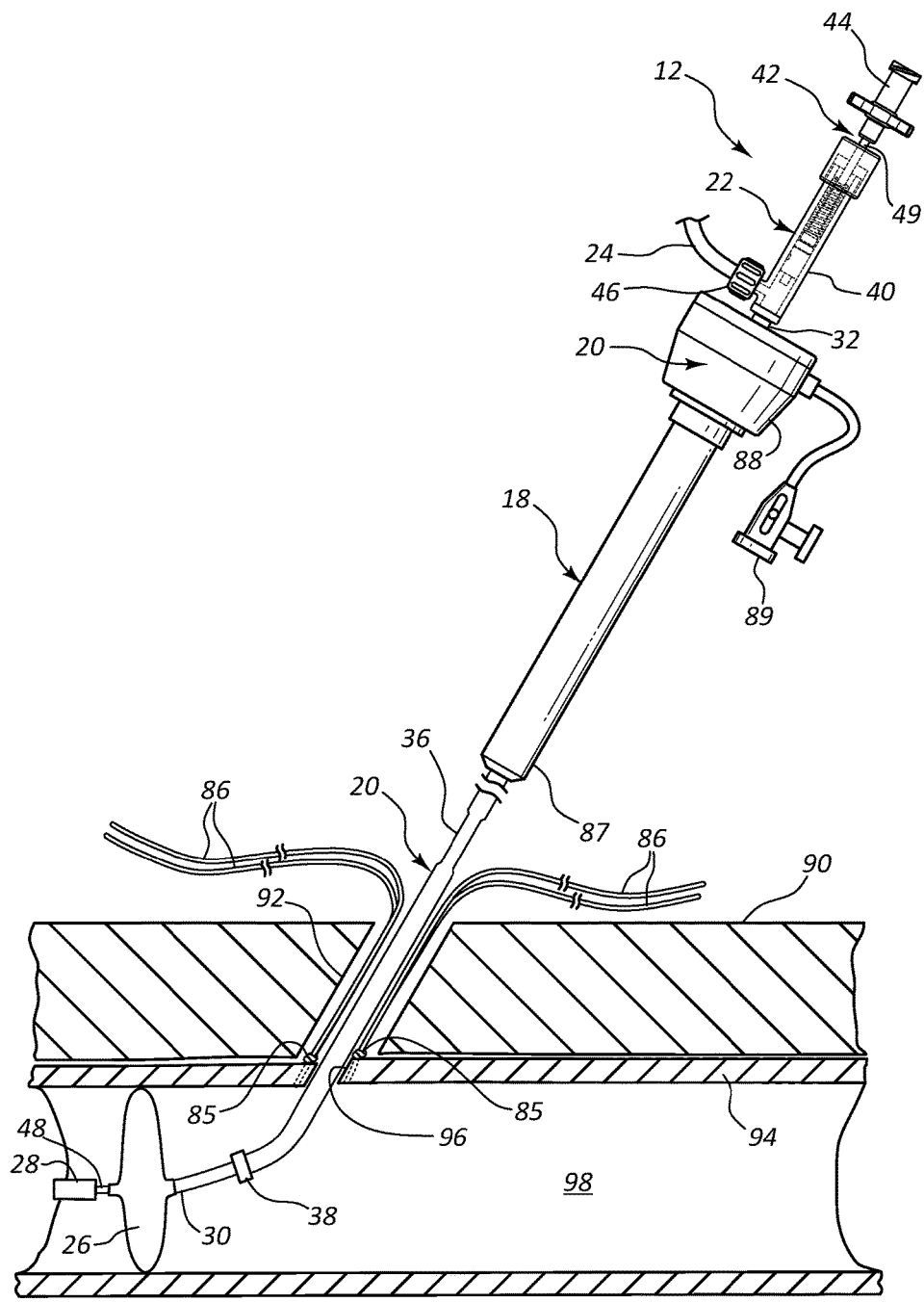
FIG. 6 shows the sheath removed from the puncture and the balloon inflation device of FIG. 5 operated to block blood flow through the vessel.

Suture knots 85 may be formed in the sutures 86 after advancing a balloon inflation device 12 through the sheath 18 and into the vessel as shown in FIGS. 6 and 7. In some arrangements the suture knots 85 are formed outside the patient and advanced along the sutures 86 to the vessel puncture after withdrawing the sheath 18 from the vessel puncture and tissue tract to improve ease of forming and advancing the suture knots 85 to their desired location to help partially close the vessel puncture. The free ends of the suture 86 may be cut within the tissue tract as shown in FIG. 7 so that the sutures do not obstruct further operation of the vascular closure system 10.

Sheath 18 may include a distal end 87, a hub 88, and an injection port 89. Typically, the sheath 18 has a width $W_3$ sufficient to expand or dilate the tissue tract and vessel puncture. The sheath 18 may be inserted into the tissue tract and vessel puncture after positioning the sutures 86 and prior to advancing the balloon inflation device 12 through the sheath 18 and into the vessel (see FIG. 5).

The inflation tube 20 may have a length sufficient to accommodate withdrawal of the sheath 18 from tissue tract 92 while balloon 26 is positioned within vessel 94 and the sheath remains distal of a proximal end of the balloon inflation device 12. Maintaining the sheath 18 positioned along the balloon inflation device 12 may reduce the complexity of handling the various devices of the vascular closure system 10 during operation. For example, the operator may avoid having to disconnect the inflation source 24 from inflation port 46 of the balloon location device 22 in order to remove sheath 18 after sheath 18 is no longer needed for the procedure of sealing vessel puncture 96. Typically, sheath 18 is moved proximally along inflation tube 20 a distance that permits attachment of the sealant delivery device 14 to balloon inflation device 12 and operation of sealant delivery device 14 without the sheath 18 obstructing such operation.

Referring now to FIGS. 2-11, an example method of sealing a vessel puncture using the vascular closure system 10 is described in detail. Referring first to FIG. 2, at least one suture is positioned across a vessel puncture 96 using suture placement device 16. The vessel puncture 96 is formed in vessel 94 and is accessible through a tissue tract 92 of a tissue layer 90.

Once extending through the vessel puncture 96, the suture placement device 16 is operated by actuating first actuator 82 to capture a wall of the vessel 94 with anchor 74. The second actuator 84 is then actuated to advance needles 78 through the wall of the vessel 94 to capture sutures 86 in the suture carrying portion 76. The second actuator 84 is actuated again to withdraw the needles 78 and sutures 86 through the vessel wall as shown in FIG. 3. The first actuator 82 is actuated to retract the anchor 74 as also shown in FIG. 3. The suture placement device 16 is then withdrawn from the vessel puncture 96 and tissue tract 92 to leave the sutures 86 placed across the vessel puncture 96 as shown in FIG. 4. Free ends of the sutures 86 may extend out of the patient for handling by the operator.

Figure 5:
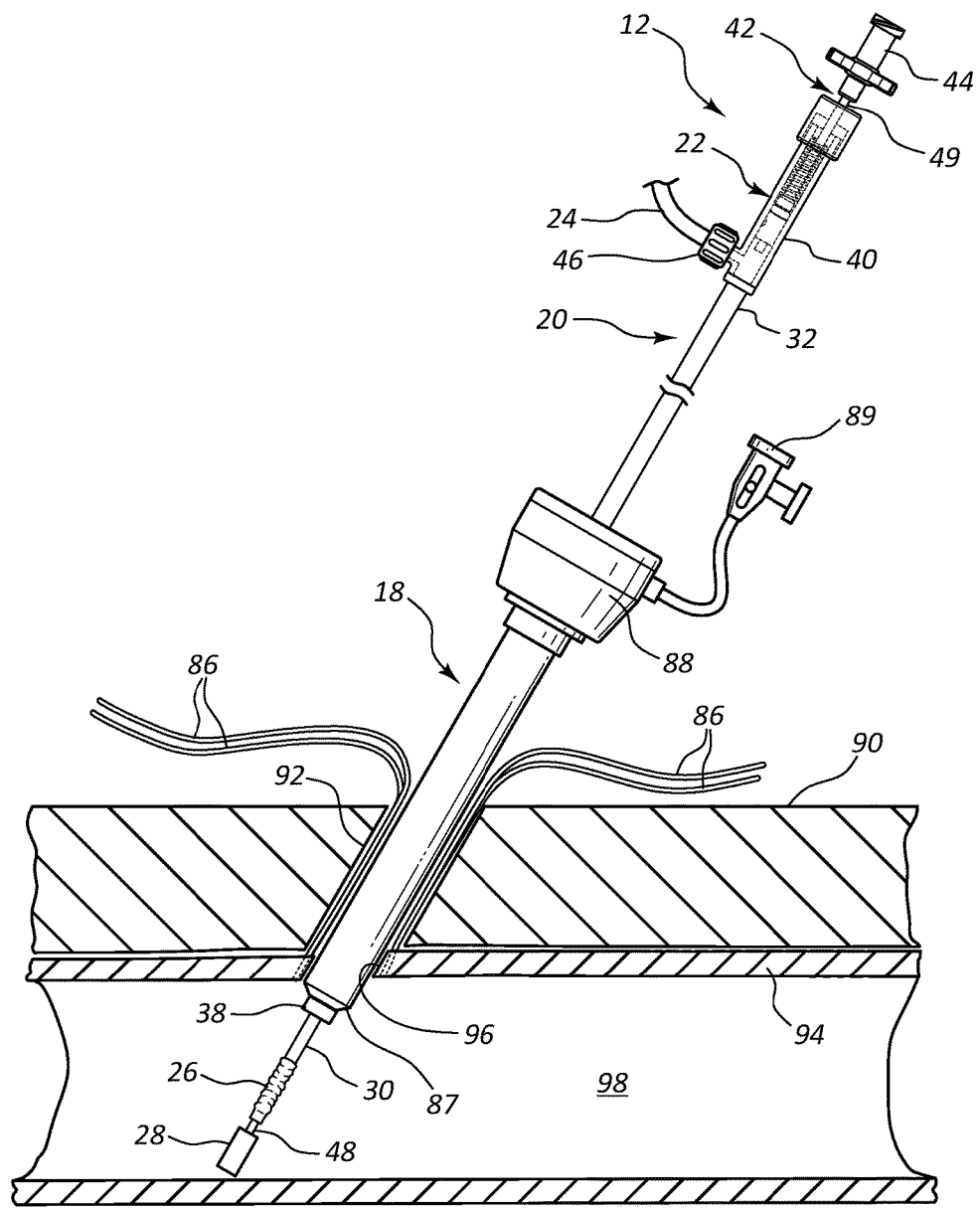
FIG. 5 shows the balloon inflation device and a sheath of the vascular closure system of FIG. 1 inserted through the puncture.

The sheath 18 is then inserted through the tissue tract 92 and vessel puncture 96 as shown in FIG. 5. The sheath 18 may expand the tissue tract 92 and vessel puncture 96. In some methods, a plurality of expansion sheaths or dilators may be inserted through the tissue tract 92 and vessel puncture 96 and removed in advance of positioning the sheath 18 as shown in FIG. 5.

The balloon inflation device 12 is advanced through the sheath 18 and into the vessel interior 98. The balloon 26 may be inflated by delivering a volume of inflation fluid via inflation source 24, which is coupled to inflation port 46 of the balloon location device 22. The inflated balloon may occlude blood flow through the vessel interior 98 as shown in FIG. 6. This temporary occlusion of the vessel 94 using balloon 26 may be referred to as a balloon bailout. This temporary occlusion of the vessel 94 may help limit blood flow through vessel puncture 96 while the operator advances suture knots 85 along the sutures 86 to the vessel puncture 96 to partially seal vessel puncture 96. Various instruments (not shown) may be used to tie and advance the suture knots 85 to the vessel puncture 96 shown in FIG. 6. A cutting device (not shown) may be used to cut the free ends of sutures 86 within tissue tract 92 so that the free ends of sutures 86 do not obstruct further operation of the vascular closure system 10. Suture locking devices may be used in place of suture knots 85 to maintain tension in the sutures 86 to help partially seal vessel puncture 96. The partial closure of vessel puncture 96 using sutures 86 or any other system or device while the balloon inflation device 12 is positioned extending through vessel puncture 96 may have advantages, particularly when balloon 26 is temporarily occluding blood flow through vessel 98.

Sheath 18 may be withdrawn proximally out of the patient prior to advancing suture knots 85. Removing sheath 18 may provide additional space for the operator to work within tissue tract 92 while advancing suture knots 85 (or suture locking devices). However, in some arrangements, sheath 18 may remain positioned at least partially within tissue tract 92 while advancing suture knots 85 to the vessel puncture 96 and cutting free ends of sutures 86.

Referring now to FIG. 7, the expanded balloon 26 is withdrawn into contact with an inner surface of the vessel 94 adjacent to and surrounding vessel puncture 96 to temporarily seal vessel puncture 96. The inflated balloon 26 may move from a first position arranged parallel with a longitudinal axis to occlude blood flow through vessel interior 98 as shown in FIG. 6, to a second position arranged generally perpendicular to a longitudinal axis of vessel 94 to occlude or seal blood flow through vessel puncture 96 as shown in FIG. 7.

Sealant delivery device 14 may be advanced through tissue tract 92 to vessel puncture 96 as shown in FIG. 7. In some arrangements, the sealant delivery device 14 is advanced along the balloon inflation device 12. In one example, a sealant delivery device 14 is mounted to balloon inflation device 12 via the exchange port 36 of inflation tube 20 and exchange lumen 58 of sealant shaft 50. Collar 38 is positioned on inflation tube 20 proximal of balloon 26 and may act as an axial position stop for sealant delivery device 14 along the balloon inflation device 12 (e.g., see FIG. 7A). Collar 38 may be positioned spaced apart axially from balloon 26 a predetermined distance that positions distal end 62 of sealant lumen 56 spaced apart from vessel puncture 96 so that the sealant flows unobstructed out of sealant delivery device 14 into tissue tract 92. The predetermined axial spacing between collar 38 and balloon 26 may be any desired amount and, in some examples, may position collar 38 either inside or outside of tissue tract 92 when balloon 26 is temporarily sealing vessel puncture 96. In some arrangements, collar 38 abuts against distal opening 64 of exchange lumen 58.

Sealant shaft 50 may be expanded by operation of expansion mechanism 60 as shown in FIG. 8. Sealant shaft 50 may expand from an unexpanded width $W_1$ as shown in FIG. 7, to an expanded width $W_2$ as shown in FIG. 8. Sealant shaft 50 may create a temporary seal with tissue tract 92 when expanded. This temporary seal may help limit backflow of sealant that is delivered by sealant delivery device 14 into tissue tract 92. In other arrangements, sealant delivery device 14 is operable without an expandable sealant shaft 50.

Figure 9:
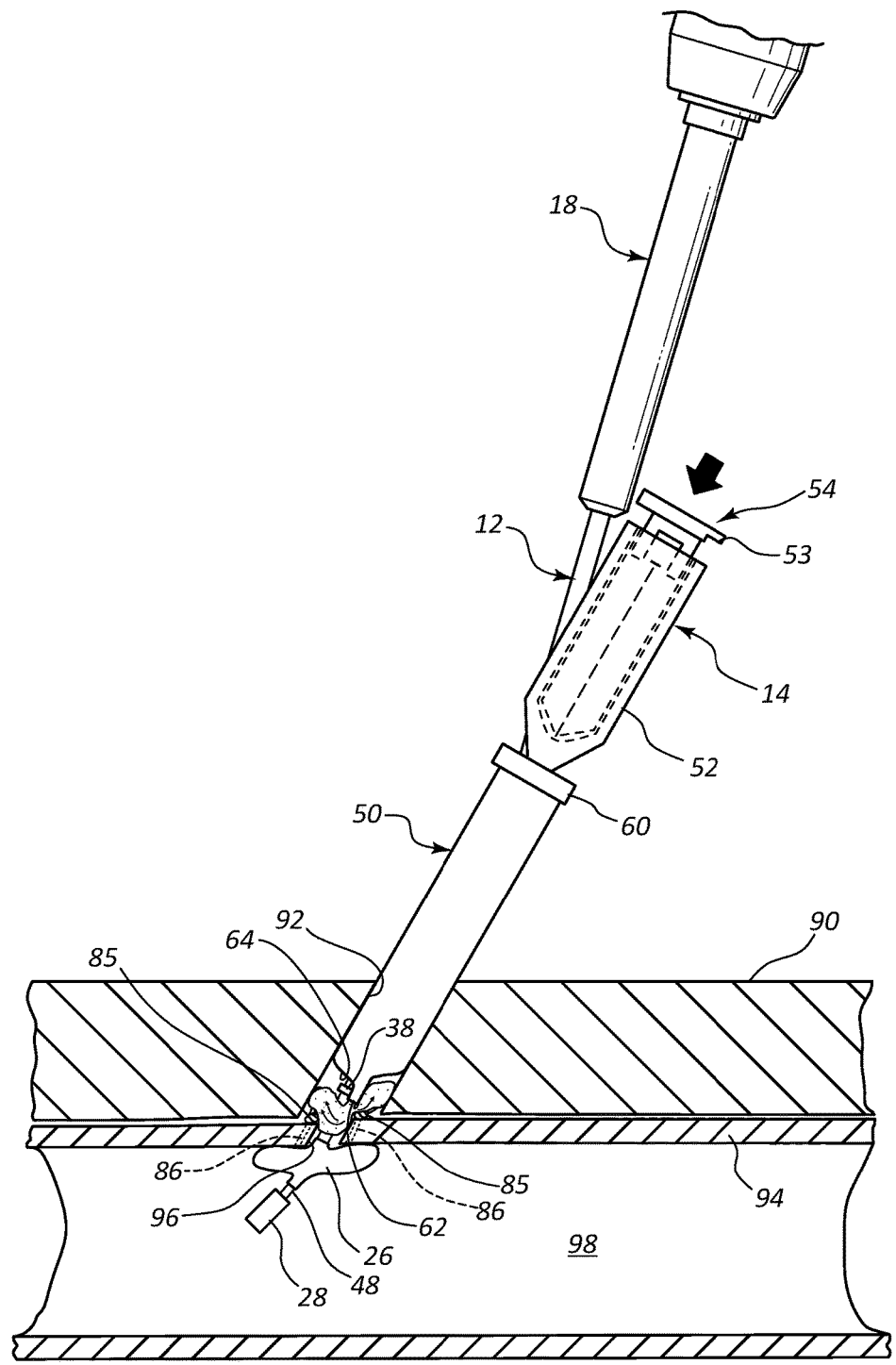
FIG. 9 shows the sealant delivery device of FIG. 8 operated to deliver a sealant to the puncture.
Figure 10:
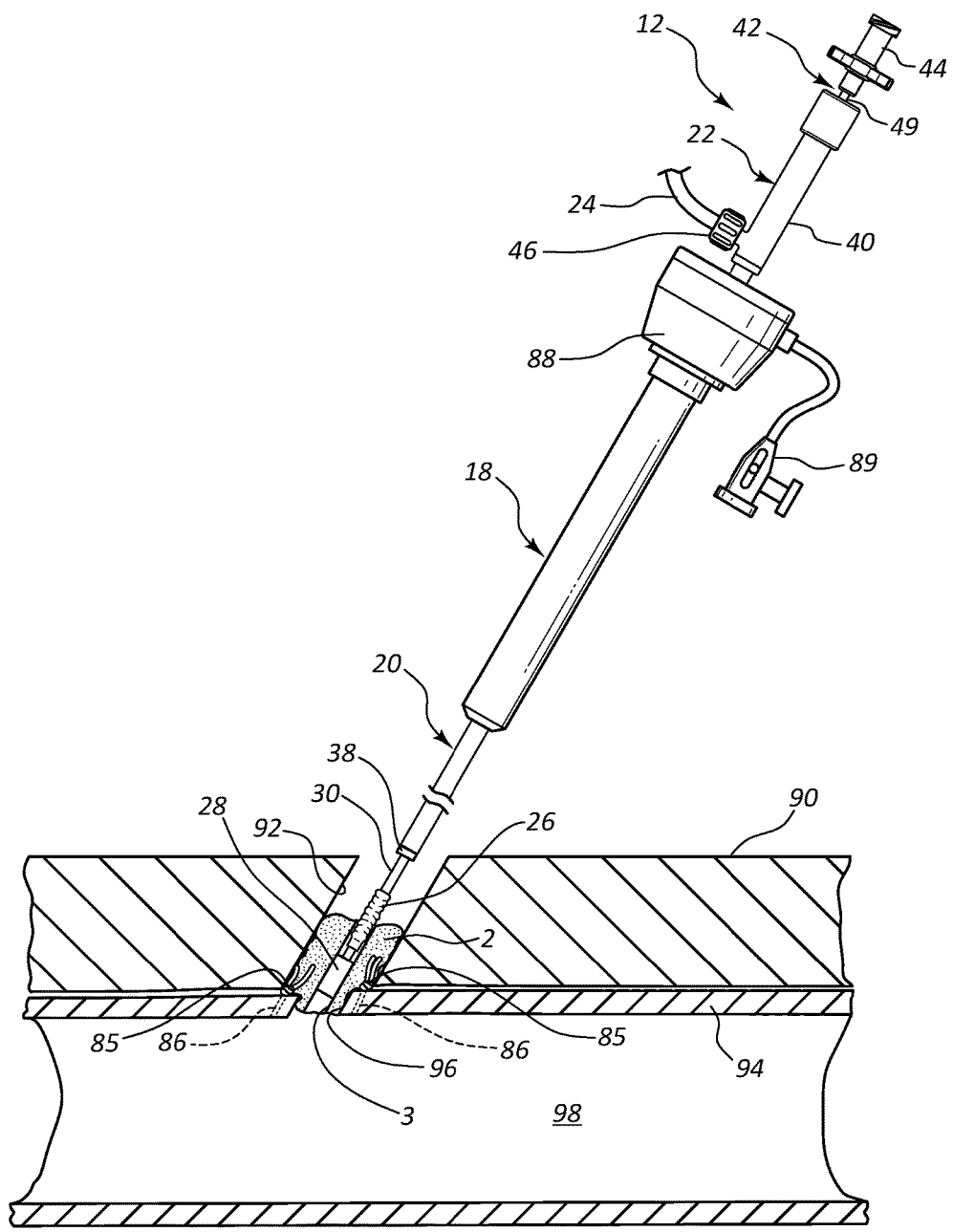
FIG. 10 shows the balloon inflation device of FIG. 1 operated to deposit a detachable tip within the sealant.

FIG. 9 shows the sealant delivery device 14 being operated to deliver a volume of sealant into tissue tract 92. The sealant mixing device 54 may be actuated distally (e.g., by advancing plunger 53) to deliver a sealant out of the distal end 62 of the sealant lumen 56. The sealant may form a primary sealant plug 2 as shown in FIG. 10. Primary sealant plug 2 may at least partially fill tissue tract 92. Primary sealant plug 2 may also at least partially seal vessel puncture 96. The inflated balloon 26 may limit the flow of the sealant into vessel interior 98.

Typically, the sealant is allowed to at least partially cure to form the primary sealant plug 2 before deflating balloon 26 and withdrawing balloon inflation device 12 through vessel puncture 96. Balloon inflation device 12 may be withdrawn until detachable tip 28 is positioned within a plug channel 3 in the primary sealant plug 2. The plug channel 3 is formed upon removal of inflation tube 20 and balloon 26 through primary sealant plug 2. Balloon inflation device 12 may be operated to detach the detachable tip 28 within the plug channel 3.

Figure 11:
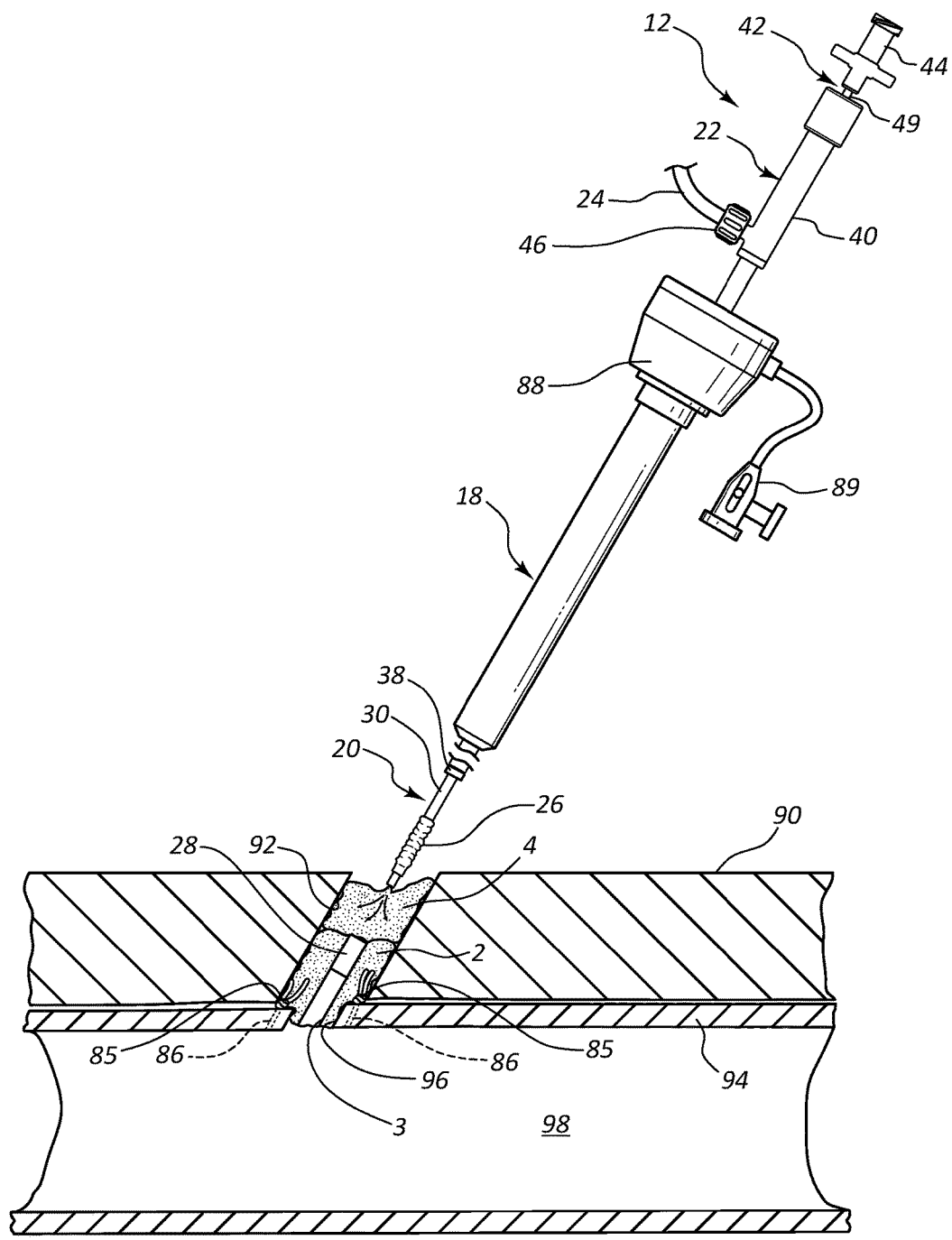
FIG. 11 shows the balloon inflation device of FIG. 1 depositing a second volume of sealant to seal the tissue tract.

A secondary volume of sealant may be deposited proximal of the primary sealant plug 2 as shown in FIG. 11. The secondary sealant may form a secondary sealant plug 4. The secondary sealant may be delivered through the inner tube 42 of the balloon location device 22. The balloon inflation device 12 may be used to deposit at least one sealant into tissue tract 92 to seal vessel puncture 96. As described above, balloon inflation device 12 may deposit two, three or more different sealing materials in the form of, for example, bioadhesive sealants delivered by the sealant delivery device 14, a detachable tip delivered by the balloon inflation device 12, or a secondary bioadhesive sealant delivered by the inner tube 42 of the balloon location device 22.

The sealant delivered by the vascular closure system 10 may be used in combination with or independent of at least partially sealing vessel puncture 96 with sutures 86 and corresponding suture knots 85. Using a combination of sutures and sealing material may be particularly effective in maintaining a sealed closure of a large bore vessel puncture, wherein sutures or sealing material independently may be less effective in maintaining closure of the vessel puncture.

The sealants discussed herein may comprise a single component, or may comprise multiple sealant components that are mixed together. The multiple sealant components may further react together to form a crosslinked network. The sealant components may be naturally derived or synthetic. Some example synthetic components include polyethers such as polyethylene glycol, polypropylene glycol and polytetrahydrofuran. Other examples of synthetic components may include polyamine compositions such as polyvinylpyrrolidones, polyethylene imines and hydrogenated polyacrylonitriles. Other example sealant components include polyacrylic and methacrylic compounds such as polyacrylic acid. Example naturally derived components include proteinaceous compositions such as albumin, collagen and polylysine. Other examples include carbohydrate compositions such polyhyaluronic acid. The sealant components may also contain reactive functional groups to promote chemical crosslinking. The sealant components may be cross-linked by any known method including, for example, condensation reactions, Michael addition, and free radical. Functional groups used for cross-linking may include, for example, thiols, acrylates, amines, succinimydyls and aldehydes, to name a few.

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A vascular closure assembly configured to seal a vascular puncture in a vessel, comprising:
    a sheath insertable to the vascular puncture;
    a balloon location device comprising:
        an inflation tube;
        an inflatable balloon positioned at a distal end of the inflation tube and operable, when inflated, between a first position blocking blood flow through the vessel and a second position sealing the vascular puncture from within the vessel, the inflation tube and the inflatable balloon being movable through the sheath to the first and second positions;
    a sealant delivery device comprising:
        a sealant delivery tube having a first lumen sized to advance over the inflation tube to the vascular puncture, and a second lumen configured to deliver a volume of sealant to the vascular puncture, the first lumen including a rapid exchange port;
        a rotatable actuator, the rotatable actuator being rotatable about a longitudinal axis of the sealant delivery device;
        an expandable portion positioned proximal of the rapid exchange port, wherein rotation of the rotatable actuator operates the expandable portion between an unexpanded position and an expanded position to create a radial seal with a percutaneous incision through which the vascular puncture is accessible;
        wherein the expandable portion of the sealant delivery device is attachable to the balloon location device entirely distal to the sheath;
    a suture placement device comprising:
        a handle;
        an anchor;
        an anchor actuator, the anchor actuator being pivotable relative to the handle and having an outer end movable between different longitudinal positions relative to the handle to expand or collapse the anchor.

2. The vascular closure assembly of claim 1, wherein the balloon location device further includes a collar positioned proximal of the inflatable balloon, the collar operating as a distal position stop for the sealant delivery device.

3. The vascular closure assembly of claim 1, wherein the balloon location device further comprises a detachable tip positioned at the distal end of the inflation tube, the detachable tip being detachable within the volume of sealant delivered to the vascular puncture upon withdrawal of the balloon location device from the vascular puncture.

4. The vascular closure assembly of claim 1, wherein the suture placement device is operable to position at least one suture across the vascular puncture prior to positioning the balloon location device within the vessel.

5. The vascular closure assembly of claim 4, wherein the suture placement device positions the at least one suture through a single sidewall of the vessel, the at least one suture extending through opposite sides of the vascular puncture adjacent to the vascular puncture, and the at least one suture is configured to be tied to partially seal the vascular puncture while the balloon location device is positioned extending through the vascular puncture.

6. The vascular closure assembly of claim 1, wherein the balloon location device comprises an exchange port, and the sheath is movable along the balloon location device to a position exposing the exchange port of the balloon location device while the inflatable balloon is in at least the second position.

7. A vascular closure assembly configured to seal a vascular puncture in a vessel, comprising:
    a balloon location device comprising:
        an inflation tube;
        an inflatable balloon positioned at a distal end of the inflation tube and operable, when inflated, between a first position blocking blood flow through the vessel and a second position sealing the vascular puncture from within the vessel;
        a collar positioned proximal of the inflatable balloon;
    a sealant delivery device comprising:
        a sealant delivery tube including:
            a first lumen sized to advance over the inflation tube to the vascular puncture, wherein a distal-facing end surface of the first lumen contacts the collar, the first lumen including a rapid exchange port;
            a second lumen configured to deliver a volume of sealant to the vascular puncture;
            an expandable portion positioned proximal of the rapid exchange port, the expandable portion being operable between an unexpanded position and an expanded position to create a radial seal with a percutaneous incision through which the vascular puncture is accessible.

8. The vascular closure assembly of claim 7, wherein the balloon location device further comprises a detachable tip positioned at the distal end of the inflation tube, the detachable tip being detachable within the volume of sealant delivered to the vascular puncture upon withdrawal of the balloon location device from the vascular puncture.

9. The vascular closure assembly of claim 7, further comprising a suture placement device operable to position at least one suture across the vascular puncture prior to positioning the balloon location device within the vessel.

10. The vascular closure assembly of claim 9, wherein the suture placement device positions the at least one suture through a single sidewall of the vessel, the at least one suture extending through opposite sides of the vascular puncture adjacent to the vascular puncture, and the at least one suture is configured to be tied to partially seal the vascular puncture while the balloon location device is positioned extending through the vascular puncture.

11. A vascular closure assembly configured to seal a vascular puncture in a vessel, comprising:
   a balloon location device comprising:
      an inflation tube;
      an inflatable balloon positioned at a distal end of the inflation tube and operable, when inflated, between a first position blocking blood flow through the vessel and a second position sealing the vascular puncture from within the vessel;
      a collar positioned proximal of the inflatable balloon;
   a sealant delivery device comprising:
      a sealant delivery tube including:
         a first lumen sized to advance over the inflation tube to the vascular puncture, wherein a distal-facing end surface of the first lumen bears against the collar, the first lumen including a rapid exchange port;
         a second lumen configured to deliver a volume of sealant to the vascular puncture;
      a rotatable actuator;
      an expandable portion positioned proximal of the rapid exchange port, wherein rotation of the rotatable actuator operates the expandable portion between an unexpanded position and an expanded position to create a radial seal with a percutaneous incision through which the vascular puncture is accessible.

12. The vascular closure assembly of claim 11, wherein the balloon location device further comprises a detachable tip positioned at the distal end of the inflation tube, the detachable tip being detachable within the volume of sealant delivered to the vascular puncture upon withdrawal of the balloon location device from the vascular puncture.

13. The vascular closure assembly of claim 11, further comprising a suture placement device operable to position at least one suture across the vascular puncture prior to positioning the balloon location device within the vessel.

14. The vascular closure assembly of claim 13, wherein the suture placement device positions the at least one suture through a single sidewall of the vessel, the at least one suture extending through opposite sides of the vascular puncture adjacent to the vascular puncture, and the at least one suture is configured to be tied to partially seal the vascular puncture while the balloon location device is positioned extending through the vascular puncture.

\* \* \* \* \*